United States Patent
Sabatucci

[11] Patent Number: 5,827,876
[45] Date of Patent: Oct. 27, 1998

[54] INHIBITION OF BONE LOSS BY 3-(4-ACRYLAMIDOBENZOYL) BENZO[B]-THIOPHENES

[75] Inventor: Joseph Peter Sabatucci, Cranbury, N.J.

[73] Assignee: American Home Products Corporation, Madison, N.J.

[21] Appl. No.: 835,435

[22] Filed: Apr. 8, 1997

Related U.S. Application Data

[60] Provisional application No. 60/015,038 Apr. 9, 1996.

[51] Int. Cl.⁶ .......................... A61K 3/445; A61K 31/38; A61K 31/385; A61K 31/40
[52] U.S. Cl. .......................... 514/448; 514/317; 514/422; 514/428; 514/435; 514/443; 514/445
[58] Field of Search ................................... 514/324, 337, 514/448

[56] References Cited

U.S. PATENT DOCUMENTS

| | | | |
|---|---|---|---|
| 4,358,593 | 11/1982 | Jones | 546/202 |
| 4,380,635 | 4/1983 | Peters | 546/202 |
| 5,441,964 | 8/1995 | Bryant | 514/324 |
| 5,457,116 | 10/1995 | Black | 514/324 |
| 5,457,117 | 10/1995 | Black | 514/337 |
| 5,461,064 | 10/1995 | Cullinan | 514/324 |

FOREIGN PATENT DOCUMENTS

WO 9701549 A of 1995 WIPO.

*Primary Examiner*—Theodore J. Criares
*Attorney, Agent, or Firm*—R. F. Boswell

[57] ABSTRACT

This invention relates to 3-(4-acrylamidobenzoyl)benzo[b] thiophenes, to the process for their preparation, to pharmaceutical compositions and to their use for modifying the balance between bone resorption and bone production in a mammal. The compounds useful in this invention are represented by the formula

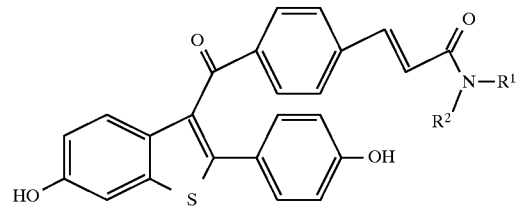

wherein $R^1$ and $R^2$ are independently hydrogen or lower alkyl containing 1–8 carbon atoms, or $R^1$ and $R^2$ together with the interposed nitrogen forms a 5–7 membered ring optionally containing an additional heteroatom selected from nitrogen, sulfur or oxygen.

14 Claims, No Drawings

INHIBITION OF BONE LOSS BY 3-(4-ACRYLAMIDOBENZOYL) BENZO[B]-THIOPHENES

This application claims priority to Provisional Application No. 60/015,038 filed on Apr. 9, 1996

FIELD OF THE INVENTION

This invention relates to 3-(4-acrylamidobenzoyl)benzo[b] thiophenes, to the process for their preparation, to pharmaceutical compositions and to their use for modifying the balance between bone resorption and bone production in a mammal.

BACKGROUND OF THE INVENTION

Osteoporosis is a common skeletal disorder affecting nearly 20 million Americans mostly over the age of 45 and resulting in 1.2 million fractures annually [S. L. Bonnick, J. Am. Med. Women's Assoc., 45, 75 (1990)]. It is thought to be caused by an imbalance between bone resorption and bone formation such that there is a net loss of bone and reduction in bone mineral density. Several kinds of osteoporosis are recognized: senile (due to aging), post-menopausal (due to estrogen-depletion following menopause), disuse (due to immobilization) and steroid-induced. Current treatments focus on preventing the bone loss with calcitonin, estrogen or bisphosphonates, ensuring an adequate supply of calcium to the bone with vitamin D and calcium or attempting to stimulate bone formation with fluoride. As formation of bone is "coupled" to previous resorption of bone, preventing bone loss can itself result in a small increase in bone mass (approx. 5%) due to the filling of resorption cavities by osteoblasts in the absence of any loss of bone elsewhere in the skeleton, a point which needs to be borne in mind when interpreting clinical data.

Treatment with sodium fluoride which is mitogenic for osteoblasts may result in bone density increase up to 8–10% a year, however, significant side-effects have also been reported, and the bone growth is irregular and fracture incidence does not appear to be significantly lowered. The class of drugs currently under development are the bisphosphonates. Treatment with these organic phosphates produces a sustained increase in bone mass for several years, but some side effects that occur are renal failure, hypotension and extra skeletal calcification.

Estrogen replacement therapy has been the treatment of choice in women. To be effective in preventing osteoporosis it may need to be taken for 5 to 10 years [Christiansen, C. Lindsay R. "Estrogens, Bone Loss and Preservation," *Osteoporosis International* 1990; 1:15–21] and this presents compliance problems as well as undesirable side effects such as edema, menstrual bleeding and potential neoplastic effects on the uterus and breast. An alternative approach is the use of estrogen-like compounds which act in some tissues as estrogen antagonists, but have lesser effects on other tissues [Black, L. J., Sato, M., Rowley, E. R. et al. Raloxifen (LY139481 HCL) prevents bone loss and reduces serum cholesterol without causing uterine hypertrophy in ovariectomized rats. *J Clin Invest* 1994, 93:63–9]

U.S. Pat. No. 4,358,593 discloses compounds of the formula

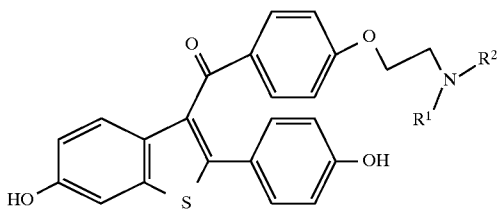

where $R^1$ and $R^2$ are independently $C_1$–$C_4$ alkyl or $NR^1R^2$ is 4-morpholinyl and which are useful for estrogenic, antiestrogenic, and antiandrogenic therapy. U.S. Pat. No. 4,380,635 describes the synthesis of 6-methoxy-2-(4-methoxyphenyl)benzo[b]thiophene, an intermediate useful in preparing the above compounds as well as compounds of this invention.

U.S. Pat. No. 5,441,964 describes bone-loss inhibiting benzo[b]thiophenes of the formula

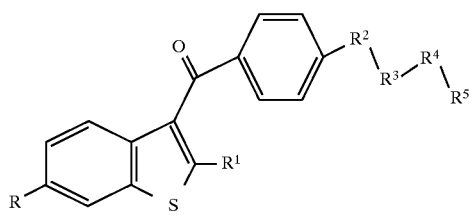

where $R^1$ is halogen, alkyl, cycloalkyl or cycloalkenyl, $R^2$ is O or $CH_2$, $R^3$ is $CH_2$ or $(CH_2)_2$, $R^4$ is carbonyl, $CH_2$ or a bond, and $R^5$ is amino, nitrilo, or an azacyclic ring optionally containing another hetero atom selected from N, O, or S. U.S. Pat. No. 5,457,117 describes bone-loss inhibiting compounds of the formula

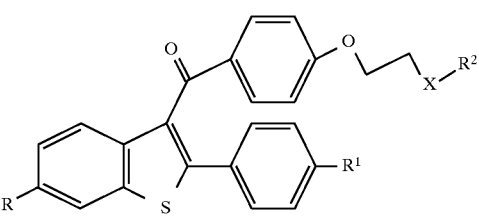

where X is a bond, $CH_2$, or $CH_2CH_2$, $R^2$ is pyrrolidine, piperidine, or hexamethyleneimino, and R and $R^1$ are, among other values, hydrogen, hydroxyl or alkoxy.

Compounds of the present invention differ from the disclosures in the above-cited US patents in three ways: (1) there is no ether oxygen in the benzoyl group side chain, (2) there is no basic nitrogen present in the benzoyl side chain, and (3), the side chain in the invention compounds is an acrylamide moiety, previously unknown in the 3-benzoyl-2-(4-hydroxyphenyl)-6-hydroxybenzo[b]thiophene system.

SUMMARY OF THE INVENTION

This invention relates to novel 3-(4-acrylamidobenzoyl) benzo[b]thiophenes derivatives useful for inhibiting bone resorption and having the formula (I)

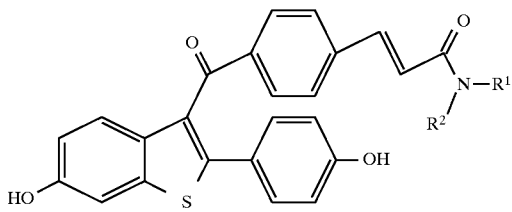

wherein $R^1$ and $R^2$ are independently hydrogen or lower alkyl containing 1–8 carbon atoms, or $R^1$ and $R^2$ together with the interposed nitrogen forms a 5–7 membered heterocyclic ring optionally containing an additional heteroatom selected from nitrogen, sulfur or oxygen.

The most preferred compounds of the present invention are:

(E)-3-{4-[6-Hydroxy-2-(4-hydroxyphenyl)benzo[b]thiophene-3-carbonyl]phenyl}-N,N-dimethylacrylamide, (E)-3-{4-[6-Hydroxy-2-(4-hydroxyphenyl)benzo[b]thiophene-3-carbonyl]phenyl}-N,N-diethylacrylamide, (E)-3-{4-[6-Hydroxy-2-(4-hydroxyphenyl)benzo[b]thiophene-3-carbonyl]phenyl}-N-N-butylacrylamide, (E)-3-{4-[6-Hydroxy-2-(4-hydroxyphenyl)benzo[b]thiophene-3-carbonyl]phenyl}-1-(piperidinyl)prop-2-en-1-one, and (E)-3-{4-[6-Hydroxy-2-(4 hydroxyphenyl)benzo[b]thiophene-3-carbonyl]phenyl}-1-(morpholin-4-yl)prop-2-en-1-one.

In the above definitions, the term "lower alkyl" includes both straight and branched chain hydrocarbons. The term "$R^1$ and $R^2$ together with the interposed nitrogen form a 5–7 membered heterocyclic ring optionally containing an additional heteroatom selected from nitrogen, sulfur or oxygen" includes, but is not limited to, pyrrolidine, piperidine, piperazine, morpholine, thiomorpholine, or homopiperidine.

DETAILED DESCRIPTION OF THE INVENTION

The invention compounds are prepared according to the steps outlined in Scheme 1 below.

SCHEME 1

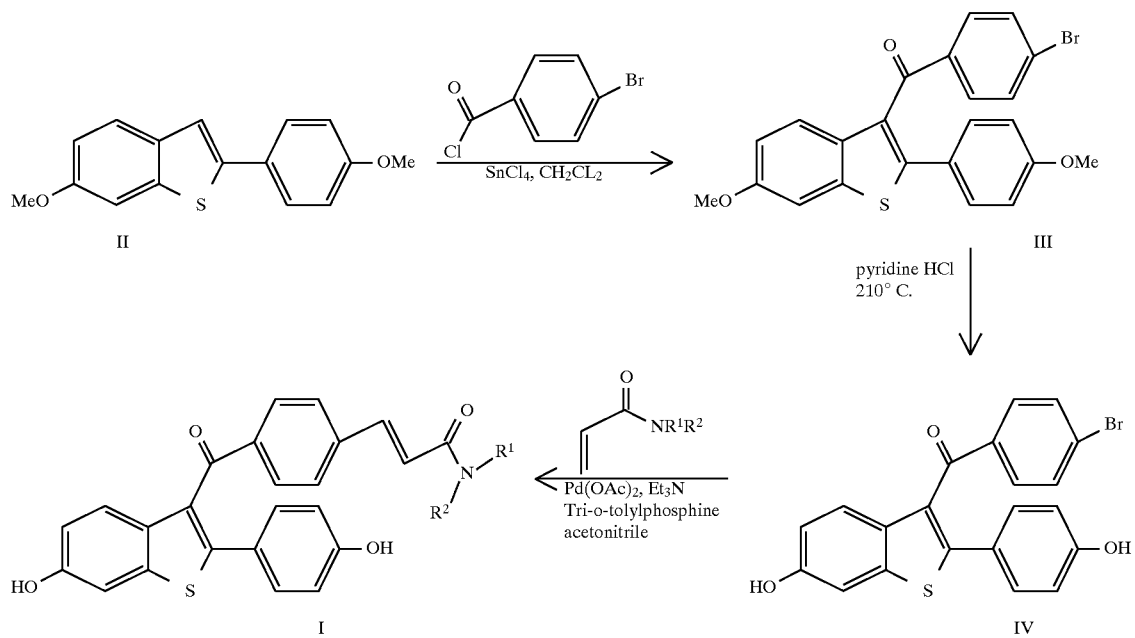

The synthesis of the title products is depicted in Scheme 1. Benzothiophenes of type (II) (prepared according to U.S. Pat. No. 4,380,635) are reacted with 4-bromobenzoyl chloride in the presence of $SnCl_4$ to provide the bromine substituted 3-benzoyl benzothiophene of type (III). This intermediate is then demethylated to provide the di-phenolic compound of type (IV) using pyridine hydrochloride or other dealkylating agents known in the art of organic synthesis. These processes are well known in the art. The title products (I) are then formed by the reaction of the appropriate acrylamide in the presence of a heavy metal catalyst and base.

The following examples are provided to illustrate the methods of preparation and testing of the compounds of the present invention. These examples are not meant to be considered, in any way, as limitations of the breadth and scope of the present invention.

EXAMPLE 1
4-Bromophenyl-[6-methoxy-2-(4-methoxy-phenyl)benzo[b]thien-3-yl]methanone To a solution of 0.54 g (2 mmol) of 6-methoxy-2-(4-methoxyphenyl)benzo-[b]thiophene and 0.52 g (2.3 mmol) of 4-bromobenzoyl chloride in 20 mL of methylene chloride at 0° C. was added dropwise a solution of 0.3 ml (2.5 mmol) of tin (IV) chloride in 5 mL of methylene chloride. After stirring for 16 hours the solution was concentrated and the residue was washed with aqueous sodium bicarbonate and extracted 2 times with 40 mL of ethyl acetate. The organic layers were combined, dried ($MgSO_4$) and concentrated. The crude solid was passed through a short plug of silica gel to remove residual tin salts. Elution with 30% EtOAc:hexane and concentration yielded 0.65 g (73%) of yellow crystals, m.p. 127°–129° C.

NMR (300 MHz, $CDCl_3$) δ 7.61(m, 3H, ArH and H4), 7.39 (d, J=8 Hz, 2H, ArH), 7.32 (d, J=2 Hz, 1H, H7), 7.27 (d, J=8 Hz, 2H, ArH), 6.99 (dd, $J_1$=2 Hz, $J_2$=8 Hz, 1H, H5), 6.74 (d, J=8 Hz, 2H, ArH), 3.89 (s, 3H, OMe), 3.75 (s, 3H, OMe).

EXAMPLE 2
4-Bromophenyl-[6-Hydroxy-2-(4-hydroxyphenyl)benzo[b]thien-3-yl]methanone To a 100 mL flask is added 1.2 g (2.7 mmol) of the product from Example 1 and 5.5 g (47.8 mmol) of pyridine hydrochloride. The flask was heated for 6 hours at 190° C. under nitrogen atmosphere. At the end of this time the flask was cooled and taken up in 150 mL of water and the solid removed by filtration. The crude solid was then dissolved in ethyl acetate and passed through a short plug of silica gel eluting with 40% ethyl acetate:hexane. The filtrate was concentrated and the solid crystallized from hot chloroform:hexane to yield 0.73 g (65%) of product as a yellow solid, m.p. 233°–234° C.

NMR (400 MHz, DMSO-d6) δ 9.80 (s, 1H, OH), 9.75 (s, 1H OH), 7.55 (m, 4H, ArH), 7.39 (d, J=9 Hz, 1H, H4) 7.34 (d, J=2 Hz, 1H, H7), 7.12 (d, J=8 Hz, 2H, ArH), 6.87 (dd, $J_1$=2 Hz, $J_2$=9 Hz, 1H, H5), 6.64 (d, J=8 Hz, 2H, ArH)

Anal. Calcd. for $C_{21}H_{13}BrO_3S \cdot 0.25 H_2O$: C, 58.68; H, 3.17. Found: C, 58.66; H, 3.01.

EXAMPLE 3
(E)-3-{4-[6-Hydroxy-2-(4-hydroxyphenyl)benzo[b]thiophene-3-carbonyl]phenyl}-N,N-dimethylacrylamide To a screw cap seal tube is added 0.84 g (2.0 mmol) of the product from Example 2, 0.20 g (0.66 mmol) of tri-o-tolylphosphine, 0.21 g (2.1 mmol) of N,N-dimethyl acrylamide, 0.040 g (0.2 mmol) of palladium acetate, 40 mL of acetonitrile and 4 mL of triethylamine. The solution was purged with nitrogen then capped and heated to 85° C. for 3 hours. At the end of this time, the solution was concentrated, then taken up in 100 mL of water:ethyl acetate (1:2). The organic layer was separated and the water layer extracted once with ethyl acetate. The ethyl acetate layers were combined, dried ($MgSO_4$) and concentrated an the residue subjected to column chromatography on silica. Elution with 50% ethyl acetate:hexane then ethyl acetate:hexane:isopropanol (60:35:5) yielded 0.63 g of product which was crystallized from chloroform:acetone:hexane to yield 0.47 g of product as a yellow solid, m.p. 208°–211° C.

NMR (400 MHz, DMSO-d6) δ 9.80 (s, 1H, OH), 9.72 (s, 1H, OH), 7.66 (m, 4H, ArH), 7.33 (m, 3H, ArH and C=CH), 7.24 (d, J=15 Hz, 1H, C=CH), 7.24 (d, J=8 Hz, 2H, ArH), 6.86 (dd, $J_1$=2 Hz, $J_2$=9 Hz, 1H, H5), 6.64 (d, J=8 Hz, 2H, ArH) 3.12 (s,3H, $NCH_3$), 2.90 (s, 3H, $NCH_3$).

Anal. Calcd. for $C_{26}H_{21}NO_4S$: C, 70.41; H, 4.77; N, 3.16. Found: C, 70.16; H, 5.01; N, 2.92.

EXAMPLE 4
(E)-N-t-Butyl-3-{4-[6-hydroxy-2-(4-hydroxyphenyl)benzo[b]thiophene-3-carbonyl]phenyl}acrylamide To a screw cap seal tube is added 0.83 g (2.0 mmol) of the product from Example 2, 0.25 g (0.82 mmol) of tri-o-tolylphosphine, 0.27 g (2.1 mmol) of t-butyl acrylamide, 0.045 g (0.21 mmol) of palladium acetate, 40 mL of acetonitrile and 4 mL of triethylamine. The solution was purged with nitrogen then capped and heated to 85° C. for 3 hours. At the end of this time, the solution was concentrated, then taken up in 100 mL of water:ethyl acetate (1:2). The organic layer was separated and the water layer extracted once with ethyl acetate. The ethyl acetate layers were combined, dried ($MgSO_4$) and concentrated an the residue subjected to column chromatography on silica. Elution with 50% ethyl acetate:hexane yielded 0.45 g of product which was crystallized from acetone:chloroform:hexane to obtain 0.34 g of yellow powder, m.p. 187°–190° C. (softening).

NMR (400 MHz, DMSO-d6) δ 9.79 (s, 1H, OH), 9.71 (s, 1H, OH), 7.76 (s, 1H, NH), 7.66 (d, J=8 Hz, 2H, ArH), 7.48 (d, J=8 Hz, 2H, ArH), 7.36 (d, J=9 Hz, 1H, H5), 7.35 (d, J=2 Hz, 1H, H7), 7.28 (d, J=15 Hz, 1H, C=CH), 7.13 (d, J=8 Hz, 2H, ArH), 6.88 (dd, $J_1$=8 Hz, $J_2$=2 Hz, 1H, H5), 6.68 (d, J=15 Hz, 1H C=CH), 6.63, (d, J=8 Hz, 2H, ArH), 1.29 (s, 9H, $C(CH_3)_3$)

Anal. Calcd. for $C_{28}H_{25}NO_4S$: C, 71.32; H, 5.34; N, 2.97. Found: C, 70.98; H, 5.41; N, 2.68.

EXAMPLE 5
(E)-N,N-Diethyl-3-{4-[6-hydroxy-2-(4-hydroxyphenyl)benzo[b]thiophene-3-carbonyl]phenyl}acrylamide To a screw cap seal tube is added 0.83 g (2.0 mmol) of the product from Example 2, 0.25 g (0.82 mmol) of tri-o-tolylphosphine, 0.30 g (2.3 mmol) of N,N-diethyl acrylamide, 0.045 g (0.21 mmol) of palladium acetate, 40 mL of acetonitrile and 4 mL of triethylamine. The solution was purged with nitrogen then capped and heated to 85° C. for 15 hours. At the end of this time, the solution was concentrated, then taken up in 100 mL of water:ethyl acetate (1:2). The organic layer was separated and the water layer extracted once with ethyl acetate. The ethyl acetate layers were combined, dried ($MgSO_4$) and concentrated. The residue subjected to column chromatography on silica. Elution first with 60% ethyl acetate:hexane followed by ethyl acetate:hexane:isopropanol (60:35:5) yielded 0.52 g of product (55%) which was crystallized from chloroform:acetone:hexane mp 159°–163° C. (soft).

NMR (400 MHz, DMSO-d6) δ 9.79 (s, 1H, OH), 9.72 (s, 1H, OH), 7.66 (s, 4H, ArH), 7.41 (d, J=15 Hz, 1H, C=CH), 7.35 (d, J=8 Hz, 1H, H4), 7.34 (s, 1H, H7), 7.15 (d, J=15 Hz, 1H, C=CH), 7.12 (d, J=8 Hz, 2H, ArH), 6.86 (dd, $J_1$=8 Hz, $J_2$=2 Hz, 1H, H5), 6.63 (d, J=8 Hz, 2H, ArH), 3.48 and 3.35 (q, J=7 Hz, 2H, $NCH_2$), 1.12 and 1.08 (t, J=7 Hz, 3H, $CH_3$).
Anal. Calcd. for $C_{28}H_{25}NO_4S$: C, 71.32; H, 5.34; N, 2.97
Found: C, 71.63; H, 4.99; N, 2.69

EXAMPLE 6
(E)-3-{4-[6-Hydroxy-2-(4 hydroxyphenyl)benzo[b]thiophene-3-carbonyl]-phenyl}-1-(morpholin-4-yl)prop-2-en-1-one To a screw cap seal tube is added 0.56 g (1.3 mmol) of the product from Example 2, 0.21 g (0.69 mmol) of tri-o-tolylphosphine, 0.25 g (1.7 mmol) of N-morpholinyl acrylamide, 0.035 g (0.15 mmol) of palladium acetate, 40 mL of acetonitrile and 4 mL of triethylamine. The solution was purged with nitrogen then capped and heated to 85° C. for 16 hours. At the end of this time, the solution was concentrated, then taken up in 100 mL of water:ethyl acetate (1:2). The organic layer was separated and the water layer extracted once with ethyl acetate. The ethyl acetate layers were combined, dried ($MgSO_4$) and concentrated an the residue subjected to column chromatography on silica. Elution first with 60% ethyl acetate:hexane followed by ethyl acetate:hexane:isopropanol (60:35:5) yielded 0.44 g (70%) of yellow solid which was crystallized from a mixture of chloroform:acetone:hexane mp 269°–271° C.
NMR (400 MHz, DMSO-d6) δ 9.80 (s, 1H, OH), 9.72 (s, 1H, OH), 7.66 (q, J=5 Hz, 4H, ArH), 7.43 (d, J=15 Hz, 1H, C=CH), 7.37 (d, J=8 Hz, 1H, H4), 7.35 (d, J=2 Hz, 1H, H7), 7.28 (d, J=15 Hz, 1H, C=CH), 7.13 (d, J=8 Hz, 2H, ArH), 6.87 (dd, $J_1$=8 Hz, $J_2$=2 Hz, 1H, H5), 6.63 (d, J=8 Hz, 2H, ArH), 3.68 (bs, 2H, $NCH_2$), 3.50–3.61 (m, 6H, $NCH_2$ and $(CH_2)_2O$).
Anal. Calcd. for $C_{28}H_{23}NO_5S.0.75 H_2O$: C, 67.39; H, 4.95; N, 2.80
Found: C, 67.53; H, 4.59; N, 2.78

EXAMPLE 7
(E)-3-{4-[6-Hydroxy-2-(4-hydroxyphenyl)benzo[b]thiophene-3-carbonyl]phenyl}-1-(piperidinyl)prop-en-1-one.

To a screw cap seal tube is added 0.63 g (1.5 mmol) of the product from Example 2, 0.21 g (0.69 mmol) of tri-o-tolylphosphine, 0.25 g (1.7 mmol) of N-piperidinyl acrylamide, 0.035 g (0.15 mmol) of palladium acetate, 40 mL of acetonitrile and 4 mL of triethylamine. The solution was purged with nitrogen then capped and heated to 85° C. for 15 hours. At the end of this time, the solution was concentrated, then taken up in 100 mL of water:ethyl acetate (1:2). The organic layer was separated and the water layer extracted once with ethyl acetate. The ethyl acetate layers were combined, dried ($MgSO_4$) and concentrated an the residue subjected to column chromatography on silica. Elution first with 60% ethyl acetate:hexane followed by ethyl acetate:hexane:isopropanol (60:35:5) yielded 0.36 g of product (50%), which was crystallized from chloroform:acetone:hexane, mp 254°–256° C.
NMR (400 MHz, DMSO-d6) δ 9.80 (s, 1H, OH), 9.71 (s, 1H, OH), 7.66 (q, J=5 Hz, 4H, ArH), 7.38 (d, J=15 Hz, 1H, C=CH), 7.35 (d, J=8 Hz, 1H, H4), 7.34 (d, J=2 Hz, 1H, H7), 7.30 (d, J=15 Hz, 1H, C=CH), 7.14 (d, J=8 Hz, 2H, ArH), 6.86 (dd, $J_1$=8 Hz, $J_2$=2 Hz, 1H, H5), 6.63 (d, J=8 Hz, 1H, ArH), 3.60 (bs, 2H, NCH2), 3.51 (bs, 2H, $NCH_2$), 1.60 (m, 2H, $CH_2$), 1.46 (m, 4H, $CH_2$).
Anal. Calcd. for $C_{29}H_{25}NO_4S.1 H_2O$: C, 69.44; H, 5.43; N, 2.79
Found: C, 69.30; H, 5.09; N, 2.71

PHARMACOLOGY
Estrogen Receptor Binding/Competition Assay
Receptor Preparation:

Chinese Hamster Ovary (CHO) cells overexpressing the estrogen receptor are grown in 150 $mm^2$ dishes in DMEM+ 10% dextran coated charcoal, stripped fetal bovine serum. The plates are washed twice with PBS and once with 10 mM Tris-HCl, pH 7.4, 1 mM EDTA. Cells are harvested by scraping the surface and then the cell suspension is placed on ice. Cells are disrupted with a hand-held motorized tissue grinder using two, 10-second bursts. The crude preparation is centrifuged at 12,000×g for 20 min. followed by a 60 min spin at 100,000×g to produce a ribosome-free cytosol. The cytosol is frozen and stored at −80° C. Protein concentration of the cytosol is estimated using the BCA assay with reference standard protein.

Binding assay conditions:

The competition assay is performed in a 96-well plate (polystyrene*) which binds <2.0% of the total input [$^3$H]-17β-estradiol. Each data point is gathered in triplicate. 100 μg/100 μl of the receptor preparation is aliquoted per well. A saturating dose of 2.5 nM [$^3$H]17β-estradiol+competitor (or buffer) in a 50 μl volume is added in the preliminary competition when 100× and 500× competitor concentrations are evaluated. For an $IC_{50}$ determination, where 12 concentrations of competitor are evaluated, only 0.8 nM [$^3$H]17β-estradiol is used. The plate is incubated at room temperature for 2.5 hours. At the end of this incubation period 150 μl of ice-cold dextran coated charcoal (5% activated charcoal coated with 0.05% 69K dextran) is added/well and the plate is immediately centrifuged at 900×g for 5 minutes at 4° C. A 200 μl sample of the supernatant solution is removed for scintillation counting. Samples are counted to 2% or 10 min, whichever occurs first.

(*Because polystyrene absorbs a small amount of [$^3$H]17β-estradiol, wells containing radioactivity and cytosol, but not processed with charcoal, are included to quantitate the amount of available isotope. Also, wells containing radioactivity but no cytosol are processed with charcoal to estimate unremovable DPM of [$^3$H]17β-estradiol. Corning #25880-96 ninety-six well plates were used as they have been determined bind the least amount of estradiol.)

Analysis of Results:

Counts per minute (CPM) of radioactivity are automatically converted to disintegrations per minute (DPM) by the Beckman LS7500 Scintillation Counter using a set of quenched standards to generate a H# for each sample. To calculate the % of estradiol binding in the presence of 100 or 500 fold competitor the following formula is applied:

DPM sample-DPM not removed by charcoal/DPM estradiol-DPM not removed by charcoal×100=% estradiol binding For the generation of $IC_{50}$ curves, % binding is plotted vs compound concentration. $IC_{50}$'s are generated for compounds that show >10% competition at up to a 500× competitor concentration.

Reference Compounds:

Various reference compounds have been evaluated and their $IC_{50}$ concentration determined. The concentration of these compounds required to displace 50% of [$^3$H]17β-estradiol is:

| | |
|---|---|
| estradiol: | 0.08 μM |
| tamoxifen: | 4.50 μM |
| raloxifene | 0.04 μM |
| 17α-dihydroequilin | 0.15 μM |

References:

Hulme, E. C., ed. (1992) Receptor-Ligand Interactions: A Practical Approach. IRL Press, New York, Chapter 8, pp 247–253.

Komm, B. S., Terpening, C. M. Benz, D. J., Graeme, K. A., Gallegos, A., Korc, M., Greene, G. L., O'Malley, B. W. and Haussler, M. R. (1988). "Estrogen Binding, Receptor mRNA and Biologic Response in Osteoblast-like Osteosarcoma Cells," Science, 241:81–84.

TABLE 1

Estrogen Receptor Binding/Competition Assay

| Example Number | $IC_{50}$ ($\mu$M) |
|---|---|
| 3 | 0.15 |
| 4 | 0.1 |
| 5 | 0.1 |
| 6 | 0.17 |
| 7 | 0.07 |

Ishikawa Cell Alkaline Phosphatase Assay

Cell maintenance and treatment:

Ishikawa cells are maintained in DMEM/F12 (50%:50%) containing phenol red+10% fetal bovine serum. The medium also is supplemented with 2 mM Glutamax, 1% Pen/Strep and 1 mM sodium pyruvate. Five days prior to the beginning of an experiment (treatment of cells) the medium is changed to phenol red-free DMEM/F12+10% dextran coated charcoal stripped serum. On the day before treatment, cells are harvested using 0.5% trypsin/EDTA and plated at a density of $5 \times 10^4$ cells/well in 96-well tissue culture plates. Test compounds are dosed at $10^{-6}$, $10^{-7}$ and $10^{-8}$M in addition to $10^{-6}$M+$10^{-9}$M 17$\beta$-estradiol to evaluate antiestrogenic activity of compounds. Cells are treated for 48 hours prior to assay. Each 96-well plate contains a 17$\beta$-estradiol control. Sample size for each compound dose is n=8.

Alkaline Phosphatase assay:

At the end of 48 hours the media is aspirated and cells are washed three times with phosphate buffered saline (PBS). 50 $\mu$l of lysis buffer (0.1M Tris-HCl, pH 9.8, 0.2% Triton X-100) is added to each well. Plates are placed at –80° C. for minimally 15 minutes. Plates are rapidly thawed at 37° C. followed by the addition of 150 $\mu$l of 0.1M Tris-HCl, pH 9.8, containing 4 mM para-nitrophenylphosphate to each well (final concentration is 3 mM pNPP). Plates are monitored at 405 nm in a microtiter plate reader (Bio-Tek, model EL340) for 1.5 h.

Analysis of Results:

Absorbance and slope calculations are done using the KineticCalc Application program (Bio-Tek Instruments, Inc., Winooski, Vt.). Results are expressed as the mean ±S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17$\beta$-estradiol.

Reference Compounds:

Various compounds were assessed for estrogenic activity by assaying for alkaline phosphatase activity and corresponding $ED_{50}$ values (95% C.I.) were calculated:

| | |
|---|---|
| 17$\beta$-estradiol | 0.03 nM (0.02–0.04 nM) |
| 17$\alpha$-estradiol | 1.42 nM (0.95–2.26 nM) |
| estriol | 0.13 nM (0.11–0.17 nM) |
| estrone | 0.36 nM (0.27–0.49 nM) |

These values agree well with in vivo rank order of potency in a rat uterotrophic assay.

References:

Holinka, C. F., Hata, H., Kuramoto, H. and Gurpide, E. (1986) "Effects of Steroid Hormones and Antisteroids on Alkaline Phosphatase Activity in Human Endometrial Cancer Cells (Ishikawa Line)," Cancer Research, 46:2771–2774.

Littlefield, B. A., Gurpide, E., Markiewicz, L., McKinley, B. and Hochberg, R. B. (1990) "A Simple and Sensitive Microtiter Plate Estrogen Bioassay Based On Stimulation Alkaline Phosphatase In Ishikawa Cells; Estrogenic Action of D5 Adrenal Steroids," Endocrinology, 6:2757–2762.

TABLE 2

Alkaline Phosphatase Assay

| Example number | Concentration (M) | % Control |
|---|---|---|
| 3 | $1 \times 10^{-6}$ | 0 |
| | $1 \times 10^{-7}$ | 0 |
| | $1 \times 10^{-8}$ | 4 |
| | $1 \times 10^{-6}$ + $1 \times 10^{-6}$ estradiol | 15 |
| 4 | $1 \times 10^{-6}$ | 2 |
| | $1 \times 10^{-7}$ | 1 |
| | $1 \times 10^{-8}$ | 0 |
| | $1 \times 10^{-6}$ + $1 \times 10^{-6}$ estradiol | 6 |
| 5 | $1 \times 10^{-6}$ | 2 |
| | $1 \times 10^{-7}$ | 2 |
| | $1 \times 10^{-8}$ | 2 |
| | $1 \times 10^{-6}$ + $1 \times 10^{-6}$ estradiol | 2 |
| 6 | $1 \times 10^{-6}$ | 2 |
| | $1 \times 10^{-7}$ | 2 |
| | $1 \times 10^{-8}$ | 2 |
| | $1 \times 10^{-6}$ + $1 \times 10^{-6}$ estradiol | 3 |
| 7 | $1 \times 10^{-6}$ | 1 |
| | $1 \times 10^{-7}$ | 2 |
| | $1 \times 10^{-8}$ | 3 |
| | $1 \times 10^{-6}$ + $1 \times 10^{-6}$ estradiol | 10 |

2X VIT ERE Transfection Assay

Cell Maintenance and treatment:

Chinese Hamster Ovary cells (CHO) which have been stably transfected with the human estrogen receptor are maintained in DMEM+10% fetal bovine serum (FBS). 48 hours prior to treatment the growth medium is replaced with DMEM lacking phenol red+10% dextran coated charcoal stripped FBS (treatment medium). Cells are plated at a density of 5000 cells/well in 96-well plates containing 200 $\mu$l of medium/well.

Calcium Phosphate Transfection:

Reporter DNA (Promega plasmid pGL2 containing two tandem copies of the vitellogenin ERE in front of the minimal thymidine kinase promoter driving the luciferase gene) is combined with the $\beta$-galactosidase expression plasmid pCH110 (Pharmacia) and carrier DNA (pTZ18U) in the following ratio:

10 $\mu$g of reporter DNA

05 $\mu$g of pCH110 DNA

05 $\mu$g of pTZ18U

20 $\mu$g of DNA/1 ml of transfection solution

The DNA (20 $\mu$g) is dissolved in 500 $\mu$l of 250 mM sterile $CaCl_2$ which is then slowly (dropwise) added to 500 $\mu$l of 2$\times$ HeBS (0.28M NaCl, 50 mM HEPES, 1.5 mM $Na_2HPO_4$, pH 7.05) and incubated at room temperature for 20 minutes. 20 μl of this mixture is added to each well of cells and remains on the cells for 16 hours. At the end of this incubation the precipitate is removed, the cells are washed with media, fresh treatment media is replaced and the cells are treated with either vehicle, 1 nM 17β-estradiol, 1 μM compound or 1 μM compound+1 nM 17β-estradiol. Each treatment condition is performed on 8 wells (n=8) which are incubated for 24 h prior to luciferase assay.

Luciferase Assay:

After 24 h exposure to compounds, the media is removed and each well is washed 2× with 125 μl of PBS lacking $Mg^{++}$ and $Ca^{++}$. After removing the PBS, 25 μl of Promega lysis buffer is added to each well and allowed to stand at room temperature for 15 min, followed by 15 min at −80° C. and 15 min at 37° C. 20 μl of lysate is tranferred to an opaque 96-well plate for luciferase activity evaluation and the remaining lysate (5 μl) is used for β-galactosidase activity evaluation (normalize transfection). The luciferan substrate (Promega) added is 100 μl aliquots to each well automatically by the luminometer and the light produced (relative light units) is read 10 seconds after addition. The data is logged and automatically sent to a JMP statistical program for analysis. A hard copy printout is also produced at the time of the assay.

β-galactosidase Assay:

To the remaining 5 μl of lysate 45 μl of PBS is added. 50 μl of Promega β-galactosidase 2× assay buffer is added, mixed well and incubated at 37° C. for 1 hour. A plate containing a standard curve (0.1 to 1.5 milliunits in triplicate) is set up for each experimental run. The plates are analyzed on a Molecular Devices spectrophotometric plate reader at 410 nm. The optical densities for the unknowns are converted to milliunits of activity by mathematical extrapolation from the standard curve.

Analysis of Results:

The luciferase data is generated as relative light units (RLUs) accumulated during a 10 second measurement and is automatically transferred to a JMP (SAS Inc) file where background RLUs are subtracted. The β-galactosidase values are automatically imported into the file and these values are divided into the RLUs to normalize the data. The mean and standard deviation is determined from a n=8 for each treatment Compound activity is compared to 17β-estradiol for each plate. Percentage of activity as compared to 17β-estradiol is calculated as follows:

$$\% \text{ Acitivity} = \frac{\text{Estradiol value} - \text{control value}}{\text{compound value}} \times 100.$$

Reference Compounds:

Various reference compounds (1 μM) were assessed for estrogenic and/or antiestrogenic activity (1 μM compound+1 nM 17β-estradiol) by assaying for luciferase activity and corresponding % values compared to 1 nM 17β-estradiol (set to 100%) were calculated. Note there are three orders of magnitude difference in the dose of reference compounds versus 17β-estradiol concentration:

| | |
|---|---|
| 17β-estradiol | 100% activity |
| estriol | 38% activity |
| estrone | 40% activity |
| tamoxifen (+1 nM estradiol) | <05% activity, (10%) |
| raloxifene (+1 nM estradiol) | <05% activity, (0%) |

At 1 μM dosages the estriol and estrone would be expected to be about 40% as potent as 17β-estradiol in this assay versus the alkaline phosphatase response in Ishikawa cells (Procedure 1501) which is a more complex biological series of events. The lack of independent activity and antiestrogenic activity of tamoxifen and raloxifene was as predicted as consistent with reports in the literature relating to their effects in a rat uterotrophic assay.

References:

Tzukreman, M. T., Esty, A., Santiso-Mere, D., Danielian, P., Parker, M. G., Stein, R. B., Pike, J. W. and McDonnell, D. P. (1994) "Human Estrogen Receptor Transactivational Capacity is Determined By Both Cellular and Promoter Context and Mediated by Two Functionally Distinct Intramolecular Regions," Molecular Endocrinology, 8:21–30.

TABLE 3

β-galactosidase Assay

| Example number | Concentration (M) | % Control |
|---|---|---|
| 3 | $1 \times 10^{-6}$ | 0 |
| | $1 \times 10^{-6}$ + 1 nM estradiol | 4 |
| 4 | $1 \times 10^{-6}$ | 0 |
| | $1 \times 10^{-6}$ + 1 nM estradiol | 0 |
| 5 | $1 \times 10^{-6}$ | 2 |
| | $1 \times 10^{-6}$ + 1 nM estradiol | 1 |
| 6 | $1 \times 10^{-6}$ | 7 |
| | $1 \times 10^{-6}$ + 1 nM estradiol | 15 |
| 7 | $1 \times 10^{-6}$ | 9 |
| | $1 \times 10^{-6}$ + 1 nM estradiol | 8 |

The estrogen receptor binding/competition assay shows that the invention compounds bind competitively at estrogen receptors mush as do estradiol, tamoxifen, raloxifen, and 17α-dihydroequilin. Raloxifen has been shown to reduce bone loss without causing uterine hypertrophy. The Ishikawa Cell Alkaline Phosphatase Assay and the 2X VIT ERE Transfection Assays demonstrate that the invention compounds are antiestrogenic in both of these assays and therefore, like raloxifen, would not be likely to cause uterine hypertrophy. The invention compounds exhibit an estrogenic profile similar to the raloxifen and are therefore expected to be useful in the treatment of osteoporosis without the undesirable estrogenic effects on the uterus.

PHARMACEUTICAL COMPOSITION

Compounds of this invention may be administered neat or with a pharmaceutical carrier patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties n suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from bone density loss must be subjectively determined by the attending physician. The variables involved include the severity of the dysfunction, and the size, age, and response pattern of the patient.

Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

We claim:

1. A method for the treatment in a host mammal in order to modify the balance between the rate of bone resorption and the rate of bone formation whereby the ratio of the rate of bone resorption to the rate of bone formation in said host animal is reduced, which comprises administering to said host mammal a therapeutically effective amount of a compound of formula:

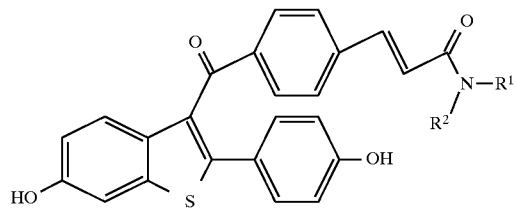

wherein $R^1$ and $R^2$ are independently hydrogen or lower alkyl containing 1–8 carbon atoms, or $R^1$ and $R^2$ together with the interposed nitrogen forms a 5–7 membered ring optionally containing an additional heteroatom selected from nitrogen, sulfur or oxygen.

2. The method according to claim 1 wherein the therapeutically effective compound used is (E)-3-{4-[6-hydroxy-2-(4-hydroxyphenyl)benzo[b]thiophene-3-carbonyl]phenyl}-N,N-dimethylacrylamide.

3. The method according to claim 1 wherein the therapeutically effective compound used is (E)-3-{4-[6-hydroxy-2-(4-hydroxyphenyl)benzo[b]thiophene-3-carbonyl]phenyl}-N,N-diethylacrylamide.

4. The method according to claim 1 wherein the therapeutically effective compound used is (E)-3-{4-[6-hydroxy-2-(4-hydroxyphenyl)benzo[b]thiophene-3-carbonyl]phenyl}-N-t-butylacrylamide.

5. The method according to claim 1 wherein the therapeutically effective compound used is (E)-3-{4-[6-hydroxy-2-(4-hydroxyphenyl)benzo[b]thiophene-3-carbonyl]phenyl}-1-(piperidinyl)prop-2-en-1-one.

6. The method according to claim 1 wherein the therapeutically effective compound used is (E)-3-{4-[6-hydroxy-2-(4 hydroxyphenyl)benzo[b]thiophene-3-carbonyl]phenyl}-1-(morpholin-4-yl)prop-2-en-1-one.

7. A compound useful for modifying the balance between the rate of bone resorption and the rate of bone formation in a host animal having the formula

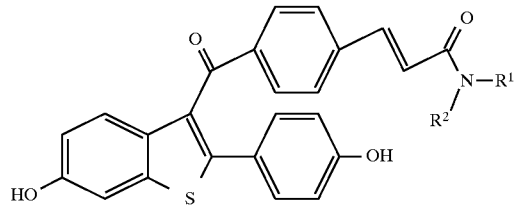

wherein $R^1$ and $R^2$ are independently hydrogen or lower alkyl containing 1–8 carbon atoms, or $R^1$ and $R^2$ together with the interposed nitrogen forms a 5–7 membered ring optionally containing an additional heteroatom selected from nitrogen, sulfur or oxygen.

8. A compound according to claim 7 which is (E)-3-{4-[6-hydroxy-2-(4-hydroxyphenyl)benzo[b]thiophene-3-carbonyl]phenyl}-N,N-dimethylacrylamide.

9. A compound according to claim 7 which is (E)-3-{4-[6-hydroxy-2-(4-hydroxyphenyl)benzo[b]thiophene-3-carbonyl]phenyl}-N,N-diethylacrylamide.

10. A compound according to claim 7 which is (E)-3-{4-[6-hydroxy-2-(4-hydroxyphenyl)benzo[b]thiophene-3-carbonyl]phenyl}-N-t-butylacrylamide.

11. A compound according to claim 7 which is (E)-3-{4-[6-hydroxy-2-(4-hydroxyphenyl)benzo[b]thiophene-3-carbonyl]phenyl}-1-(piperidinyl)prop-2-en-1-one.

12. A compound according to claim 7 which is (E)-3-{4-[6-hydroxy-2-(4 hydroxyphenyl)benzo[b]thiophene-3-carbonyl]phenyl}-1-(morpholin-4-yl)prop-2-en-1-one.

13. A process for the production of compounds of the formula

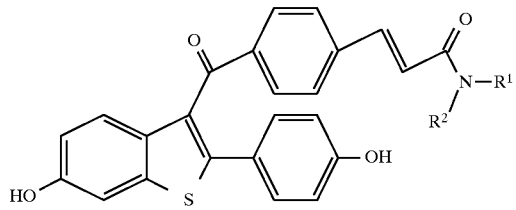

wherein $R^1$ and $R^2$ are independently hydrogen or lower alkyl containing 1–8 carbon atoms, or $R^1$ and $R^2$ together with the interposed nitrogen forms a 5–7 membered ring optionally containing an additional heteroatom selected from nitrogen, sulfur or oxygen, which comprises:
  (a) reacting 2-(4methoxyphenyl)-6-methoxybenzo[b]thiophene with 4-bromobenzoylchloride in an aprotic solvent such as methylene chloride in the presence of a metal halide catalyst such as $SnCl_4$,
  (b) heating together the 3-(4-bromobenzoyl)-2-(4-methoxyphenyl)-6-methoxyphenylbenzo[b]thiophene produced in step (a) with pyridine hydrochloride, and
  (c) reacting the 3-(4-bromobenzoyl)-2-(4-hydroxyphenyl)-6-hydroxybenzo[b]thiophene obtained in step (b) with a N-substituted or unsubstituted acrylamide in the presence of a heavy metal catalyst such as $Pd(OAc)_2$ and a base such as triethylamine with tri-O-tolylphosphine in a polar aprotic solvent such as acetonitrile.

14. A pharmaceutical composition useful for modifying the balance between the rate of bone resorption and the rate of bone formation in a host mammal whereby the ratio of said rate of bone resorption to said rate of bone formation is reduced, comprising a pharmaceutically acceptable carrier and a therapeutically effective amount of a compound of the formula

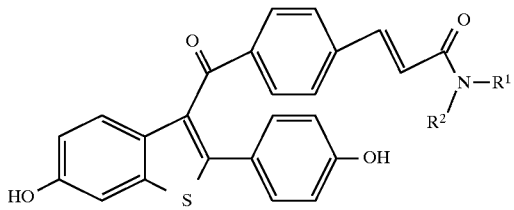

wherein $R^1$ and $R^2$ are independently hydrogen or lower alkyl containing 1–8 carbon atoms, or $R^1$ and $R^2$ together with the interposed nitrogen forms a 5–7 membered ring optionally containing an additional heteroatom selected from nitrogen or oxygen.

* * * * *